United States Patent
Qin et al.

(10) Patent No.: US 6,506,333 B1
(45) Date of Patent: *Jan. 14, 2003

(54) METHOD OF SURFACE MODIFYING A MEDICAL TUBING

(75) Inventors: Chuan Qin, Gurnee, IL (US); Patrick T. Ryan, Crystal Lake, IL (US); Michael T. K. Ling, Vernon Hills, IL (US); Donna L. Rostron, Bartlett, IL (US); Yuanpang S. Ding, Vernon Hills, IL (US); Lecon Woo, Libertyville, IL (US); Susan R. Mizener, Walworth, WI (US); Birendra K. Lal, Lake Zurich, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,518

(22) Filed: Sep. 3, 1999

Related U.S. Application Data

(63) Continuation-in-part of application No. 09/084,816, filed on May 26, 1998, now Pat. No. 6,187,400, which is a continuation-in-part of application No. 08/642,275, filed on May 3, 1996, now Pat. No. 5,932,307.

(51) Int. Cl.[7] .............................................. B29C 47/06
(52) U.S. Cl. ..................... 264/470; 264/473; 264/184; 264/211.13
(58) Field of Search ................................ 604/151, 131; 428/36.9, 36.91; 138/137, 141; 264/470, 473, 183, 184, 211.13, 211.12

(56) References Cited

U.S. PATENT DOCUMENTS 813,918 A 12/1906 Schmitz
2,551,710 A 5/1951 Slaughter (List continued on next page.)

FOREIGN PATENT DOCUMENTS

CS 250874 8/1988

(List continued on next page.)

OTHER PUBLICATIONS

*Wilpers, et al., *Functionalized Modified High Melt Flow Polyolefins*, United States Statutory Invention Registration No. H1419, Feb. 7, 1995.
*The Effect of Plastic Formulation Variables on Bond Strengths Achieved With Typical Medical Device Adhesives*, presented at Manufacturing Medical Plastics '95 by Pat Courtney, Senior Application Engineer, Loctite Corporation.
*Courtney, P., et al., *Adhesive Bonding of Medical Plastics: An Overview*, Medical Plastics and Biomaterials, Jan./Feb., 1996, pp. 20–25.
*Medical Tubes Use Metallocene Resin*, European Plastic News, Jun., 1996, p. 17.
*Extrusion Line for Medical Tubes*, Industrial & Production Engineering (PE), Dec., 1988, p. 17.

Primary Examiner—Mark Eashoo
(74) Attorney, Agent, or Firm—Mark J. Buonaiuto; Joseph A. Fuchs

(57) ABSTRACT

The present invention provides a method for fabricating a medical tubing. The method includes the steps of: (1) providing a material selected from the group consisting of ethylene homopolymers and ethylene copolymers, wherein the ethylene copolymers are obtained by copolymerizing ethylene with a comonomer selected from the group consisting of lower alkyl olefins, lower alkyl esters of a carboxylic acid and lower alkene esters of a carboxylic acid, the lower alkyl and lower alkene each have from 3–18 carbons, or blends thereof; (2) providing an extruder with an extrusion die; (3) extruding the material into a medical tubing; (4) providing a surface modifier solution; (5) preheating the surface modifier solution to a temperature within the range of 50–80° C.; and (6) applying the preheated solution onto the tubing at it exits the extrusion die when the tubing is in a molten state or a semi-molten state.

17 Claims, 6 Drawing Sheets

U.S. PATENT DOCUMENTS

| | | | |
|---|---|---|---|
| 3,157,724 A | | 11/1964 | Salyer et al. |
| 3,218,380 A | | 11/1965 | Euling et al. |
| 3,260,776 A | | 7/1966 | Lindstrom, Jr., et al. |
| 3,581,776 A | | 6/1971 | Sheahan |
| 3,775,523 A | | 11/1973 | Haley |
| 3,856,889 A | | 12/1974 | McConnell |
| 3,886,227 A | | 5/1975 | VanBrederode et al. |
| 3,974,240 A | | 8/1976 | Bock et al. |
| 4,014,369 A | | 3/1977 | Kobres, Jr. |
| 4,056,344 A | * | 11/1977 | Lemelson .................. 425/132 |
| 4,157,194 A | | 6/1979 | Takahashi |
| 4,157,235 A | | 6/1979 | Lagabe et al. |
| 4,193,899 A | | 3/1980 | Brenner et al. |
| 4,374,882 A | | 2/1983 | Harlan |
| 4,422,999 A | | 12/1983 | Mitchell |
| 4,444,817 A | | 4/1984 | Subramanian |
| 4,479,989 A | | 10/1984 | Mahal |
| 4,563,259 A | | 1/1986 | Rayner |
| 4,613,533 A | | 9/1986 | Loomis et al. |
| 4,623,567 A | | 11/1986 | Hart |
| 4,678,834 A | | 7/1987 | Boivin et al. |
| 4,698,196 A | | 10/1987 | Fabian |
| 4,721,637 A | | 1/1988 | Suzuki |
| 4,737,547 A | | 4/1988 | White |
| 4,886,634 A | | 12/1989 | Strutzel et al. |
| 4,906,496 A | | 3/1990 | Hosono et al. |
| 4,931,230 A | * | 6/1990 | Krueger et al. ............. 264/115 |
| 4,948,643 A | | 8/1990 | Mueller |
| 4,952,361 A | * | 8/1990 | Cree .......................... 264/204 |
| 4,957,974 A | | 9/1990 | Ilenda et al. |
| 5,018,945 A | | 5/1991 | D'Silva |
| 5,045,620 A | | 9/1991 | Itaba et al. |
| 5,048,572 A | | 9/1991 | Levine |
| 5,151,019 A | | 9/1992 | Danby et al. |
| 5,169,708 A | | 12/1992 | Amaral et al. |
| 5,200,130 A | * | 4/1993 | Meirowitz et al. .......... 156/167 |
| 5,225,451 A | | 7/1993 | Rogers et al. |
| 5,241,031 A | | 8/1993 | Mehta |
| 5,264,488 A | | 11/1993 | Takeuchi et al. |
| 5,274,035 A | | 12/1993 | Chundury |
| 5,281,670 A | | 1/1994 | Lee et al. |
| 5,343,738 A | | 9/1994 | Skaggs |
| 5,439,454 A | | 8/1995 | Le et al. |
| 5,525,388 A | | 6/1996 | Ward et al. |
| 5,562,127 A | | 10/1996 | Fanselow et al. |
| 5,573,822 A | | 11/1996 | Nishikawa et al. |
| 5,620,760 A | | 4/1997 | Galimberti et al. |
| 5,629,059 A | | 5/1997 | Desai et al. |
| 5,638,660 A | | 6/1997 | Kuo |
| 5,849,368 A | * | 12/1998 | Hostettler et al. ........ 427/255.4 |
| 5,932,299 A | * | 8/1999 | Katoot .................... 427/385.5 |
| 5,932,307 A | | 8/1999 | Ryan et al. |
| 6,242,041 B1 | * | 6/2001 | Katoot et al. .............. 427/2.24 |

FOREIGN PATENT DOCUMENTS

| | | |
|---|---|---|
| DE | 1 928 843 | 6/1969 |
| EP | 0 133 355 | 7/1984 |
| EP | 0 142 315 A2 | 5/1985 |
| EP | 0 142 315 | 5/1985 |
| EP | 0 256 644 | 2/1988 |
| EP | 0 450 088 A1 | 10/1991 |
| EP | 0 735 089 A2 | 10/1996 |
| EP | 0 735 089 A3 | 2/1999 |
| JP | 4-332624 | 11/1992 |
| JP | 5-017639 | 1/1993 |
| JP | 7-205275 | 8/1995 |
| JP | 7-205276 | 8/1995 |
| WO | WO 80/02671 | 12/1980 |
| WO | PCT/GB85/00197 | 5/1985 |
| WO | WO 85/05364 | * 12/1985 |
| WO | WO 92/18173 | 10/1992 |
| WO | WO 94/26793 | 11/1994 |
| WO | PCT/US95/10706 | 8/1995 |
| WO | WO 96/08520 | 3/1996 |
| WO | WO 96/36374 | 11/1996 |
| WO | 97/07032 | 4/1997 |
| WO | 97/07033 | 4/1997 |
| WO | PCT/US97/07034 | 4/1997 |
| WO | PCT/US97/07040 | 4/1997 |
| WO | WO 97/41906 | 11/1997 |
| WO | WO 97/42020 | 11/1997 |
| WO | WO 99/61083 | 12/1999 |

* cited by examiner

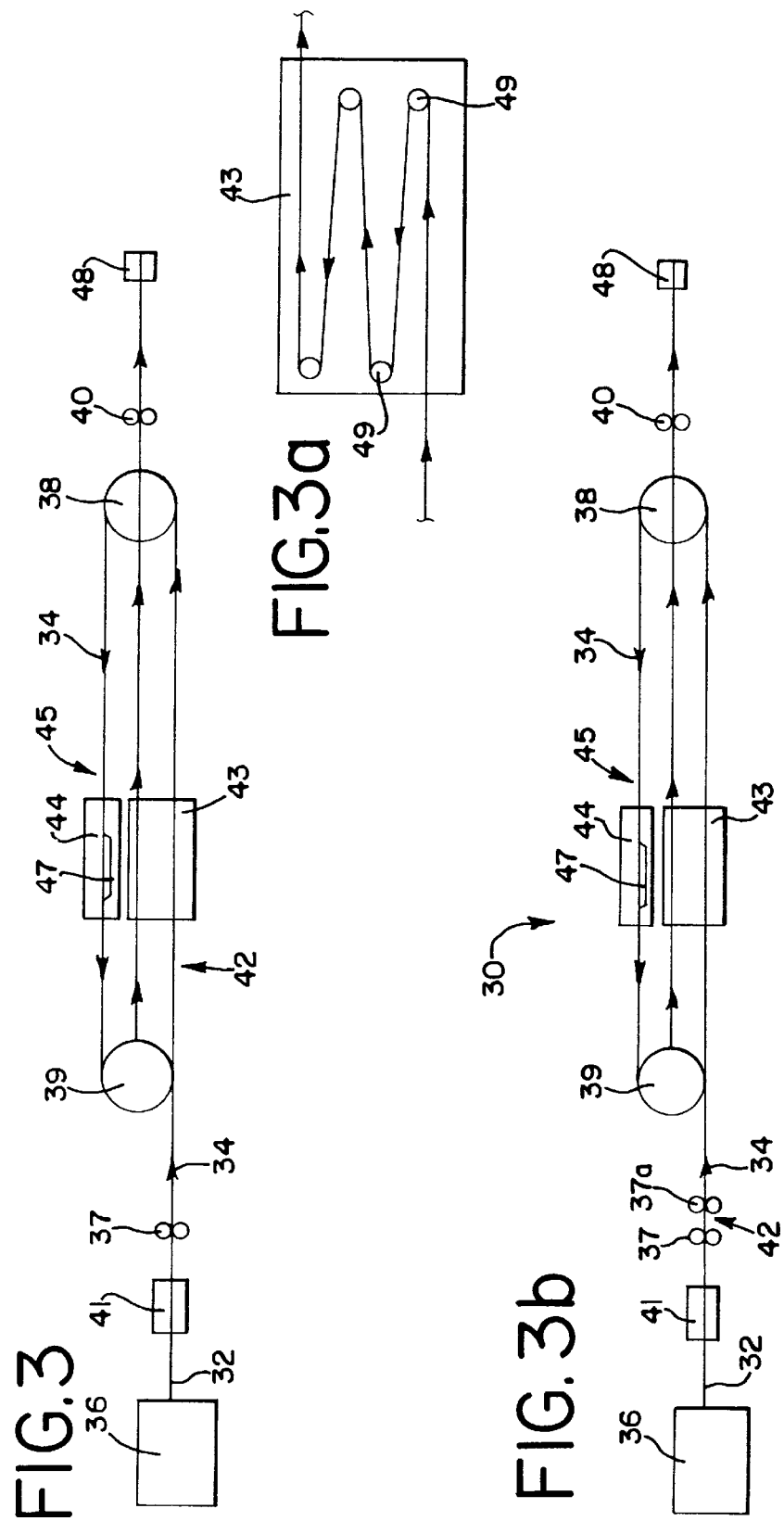

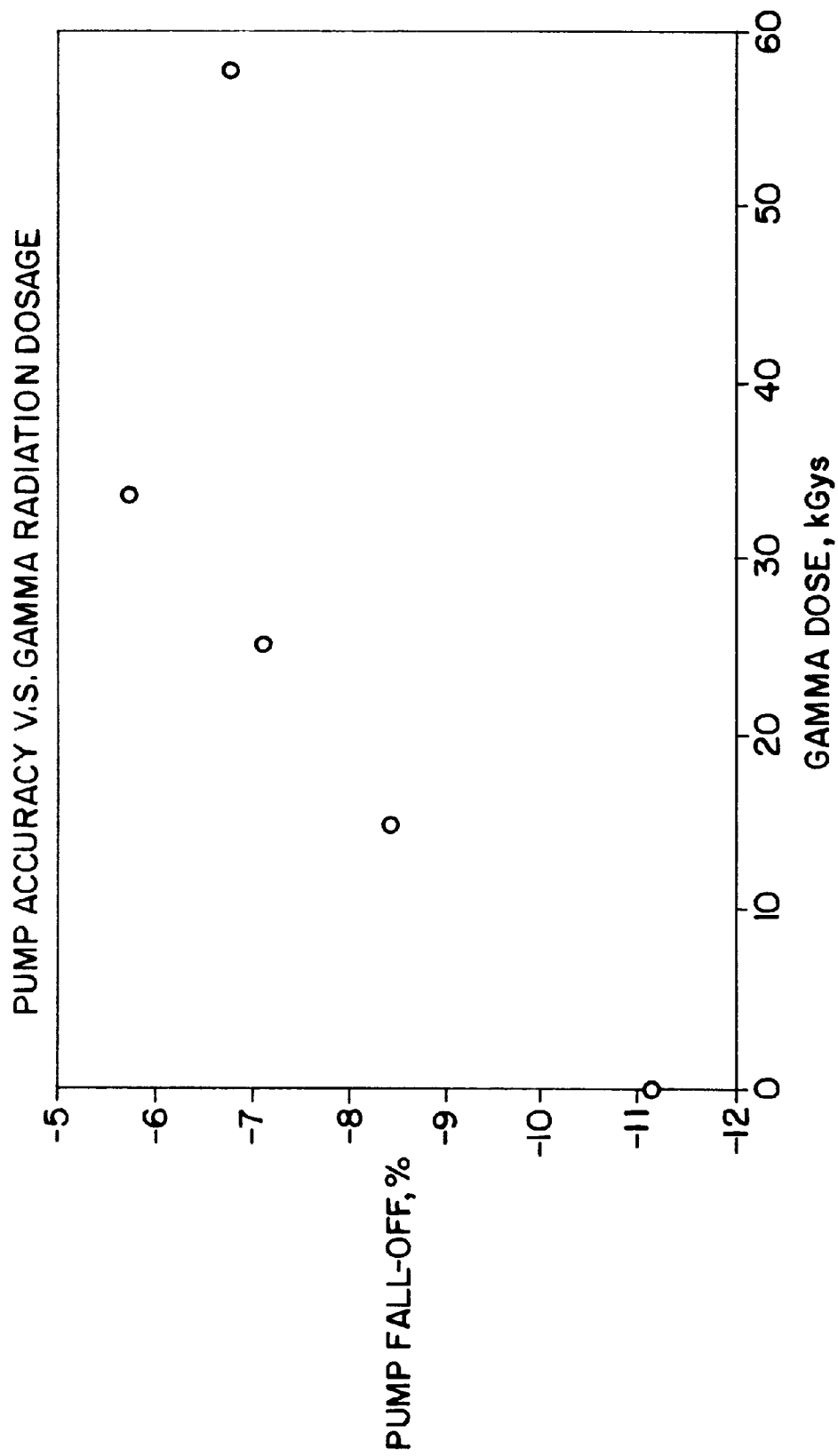

METHOD OF SURFACE MODIFYING A MEDICAL TUBING

RELATED APPLICATIONS

This application is a continuation-in-part of U.S. patent application Ser. No. 09/084,816 filed on May 26, 1998 which is a Continuation-in-part of U.S. patent application Ser. No. 08/642,275 filed on May 3, 1996 and now is U.S. Pat. No. 5,932,307. U.S. patent application Ser. No. 09/084,816 and U.S. Pat. No. 5,932,307 are hereby incorporated herein by reference, and made a part hereof.

TECHNICAL FIELD

This invention relates to a method of surface modifying a medical tubing and in particular applying a surface modifier to a polyolefin tubing to functionalize the surface of tubing for improved adhesion and to increase lubricity of the surface.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in fluid administration sets. Among these are the materials must be optically clear, environmentally compatible, have sufficient yield strength and flexibility, have a low quantity of low molecular weight additives, and be compatible with medical solutions.

It is desirable for medical tubing to be optically transparent to allow for visual inspection of fluids in the tubing.

It is also a requirement that the tubing materials be environmentally compatible as a great deal of medical tubing is disposed of in landfills and through incineration. Further benefits are realized by using a material which is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration, causing corrosion of the incinerator.

To be compatible with medical solutions, it is desirable that the tubing material be free from or have a minimal content of low molecular weight additives such as plasticizers, stabilizers and the like. These components could be extracted into the therapeutic solutions that come into contact with the material. The additives may react with the therapeutic agents or otherwise render the solution ineffective.

This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousand dollars per dose, it is imperative that the dosage not be changed.

Polyvinyl chloride ("PVC") has been widely used to fabricate medical tubings as it meets most of these requirements. However, because PVC by itself is a rigid polymer, low molecular weight components known as plasticizers must be added to render PVC flexible. As set forth above, these plasticizers may leach out of the tubing and into the fluid passing through the tubing to contaminate the fluid or to render the fluid unusable. For this reason, and because of the difficulties encountered in incinerating PVC, there is a need to replace PVC medical tubing.

Polyolefins have been developed which meet many of the requirements of medical containers and tubing, without the disadvantages associated with PVC. Polyolefins typically are compatible with medical applications because they have minimal extractability to the fluids and contents which they contact. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

For example, because of the inert nature of polyolefins, due in part to the nonpolar nature of the polymer, difficulties have been encountered in bonding the polyolefin materials to polar molecules, such as polycarbonates and acrylic polymers. Typically, medical containers such as I.V. bags are connected to a patient through a series of connected tubing that have drip chambers, Y-type injection sites, venous catheters and the like between the bag and the patient. Many of these components include rigid housings manufactured from polymers such as polycarbonates, acrylics and copolyesters. The housings have sleeves in which the tubing is inserted in a telescoping fashion to attach the tube to the housing. Therefore, it is necessary for the medical tubing to be connected to the rigid housing to form a fluid tight seal with the housings.

PVC tubing is typically secured within such housings using solvent bonding techniques. Solvent bonding requires exposing the end of the tubing to be inserted into the housing to a solvent such as cyclohexanone or methyl ethyl ketone. The solvent effectively softens or dissolves the PVC so when the tubing is inserted into the housing, a bond is formed. It is desirable that the outer tubing diameter be approximately the same dimension or slightly larger than the inner diameter of the housing to form an interference fit, as close tolerances in these dimensions assists in forming a secure bond.

Solvent bonding techniques, however, are ineffective on certain polyolefins including polyethylene. Problems have also been encountered in using adhesive bonding techniques.

One attempt at overcoming this problem was to use a two step process of applying a primer material to the surface of the tubing to be bonded followed by an adhesive. The primer was applied to the tubing when the tubing was in a solid state and when both the primer and tubing were at room temperature. Cyanoacrylate adhesives have worked with some success using this technique with a primer. However, the two step process adds an additional step to a manufacturing process which could slow down the production line and increase the labor costs. Further, primers increase the cost of the process. Third, because primers typically contain large quantities of volatile chemicals such as organic solvents, and might lead to toxicity, safety and environmental problems. Fourth, primers may limit manufacturing options as they have a limited on-part life time, i.e., the primers will lose their activities within hours after exposure to an ambient environment. Finally, prior surface coating techniques have not adequately provided for both modifying the tubing surface for both increasing the adhesive compatibility with polar adhesives while at the same time lubricating the surface of the tubing for slide clamp compatibility and medical infusion pump compatibility.

In U.S. patent application Ser. No.08/642,278, the additives were blended directly into the polyolefin material. This procedure was suitable for modifing the outer surface of monolayer and multiple layered tubing as the low molecular weight additives migrated to the outer surface of the tubing. However, one drawback encountered was that for the monolayered tubings the additives also could possibly migrate to the inner surface of the tubing where they were exposed to the infusion pathway where they could leach out into the liquids flowing through the tubing.

The present invention solves these and other problems.

DISCLOSURE OF INVENTION

The present invention provides a process for modifying the surface of a polyolefin medical tubing for increasing the compatibility of the tubing with adhesives and increasing the surface lubricity of the tubing.

The present invention provides a method for fabricating a medical tubing. The method includes the steps of: (1) providing a material selected from the group consisting of ethylene homopolymers and ethylene copolymers, wherein the ethylene copolymers are obtained by copolymerizing ethylene with a comonomer selected from the group consisting of lower alkyl olefins, lower alkyl esters of a carboxylic acid and lower alkene esters of a carboxylic acid, the lower alkyl and lower alkene each have from 3–18 carbons, or blends thereof; (2) providing an extruder with an extrusion die;

(3) extruding the material into a medical tubing; (4) providing a surface modifier solution; (5) preheating the surface modifier solution to a temperature within the range of about 30–95° C.; and (6) applying the preheated solution onto the tubing at it exits the extrusion die when the tubing is in a molten state or a semi-molten state.

The present invention further provides a method of using a medical tubing with a pump for administering measured amounts of a beneficial fluid over time to a patient. The method includes the steps of: (1) providing a material selected from the group consisting of ethylene homopolymers and ethylene copolymers, wherein the ethylene copolymers are obtained by copolymerizing ethylene with a comonomer selected from the group consisting of lower alkyl olefins, lower alkyl esters of a carboxylic acid and lower alkene esters of a carboxylic acid, the lower alkyl and lower alkene each have from 3–18 carbons, or blends thereof; (2) providing an extruder with an extrusion die; (3) extruding the material into a medical tubing; (4) providing a surface modifier solution; (5) preheating the surface modifier solution to a temperature within the range of 30–95° C.; (6) applying the preheated solution onto the tubing at it exits the extrusion die when the tubing is in a molten state or a semi-molten state; and (8) pumping fluid through the tubing with the pump.

The present invention further provides a method of fabricating a multilayered medical tubing including the steps of: (1) extruding a multilayered tubing having a first layer and a second layer, the first layer of an ethylene monomer copolymerized with at least one monomer selected from the group consisting of lower alkyl esters of a carboxylic acid and lower alkene esters of a carboxylic acid, the lower alkyl and the lower alkene each have from 3–10 carbons, the second layer of homopolymers and copolymers of alpha olefins, the second layer being disposed concentrically within the first layer and having a modulus of elasticity greater than a modulus of elasticity of the first layer, (2) providing a surface modifier solution; (3) preheating the surface modifier solution to a temperature within the range of 50–80° C.; and (4) applying the preheated solution onto the tubing at it exits the extrusion die when the tubing is in a molten state or a semi-molten state.

The present invention further provides a method for fabricating medical tubing including the steps of: (1) extruding with an extruder having an extrusion die a tubing having a first layer selected from the group consisting of ethylene homopolymers and ethylene copolymers, wherein the copolymers of ethylene are an ethylene monomer copolymerized with at least one monomer selected from the group consisting of lower alkyl olefins having from 3 to 18 carbons, lower alkyl esters of a carboxylic acid, the lower alkyl having from 3 to 18 carbons, and lower alkene esters of a carboxylic acid, the lower alkene having from 3 to 18 carbons, (2) providing a surface modifier solution; (3) preheating the surface modifier solution to a temperature within the range of 50–80° C.; (3) applying the preheated solution onto the tubing at it exits the extrusion die when the tubing is in a molten state or a semi-molten state; (4) cooling the tubing to a solid state to define an initial diameter; and (5) stretching the tubing in a direction along a longitudinal axis of the tubing to define an oriented diameter that is less than the initial diameter; and (6) heat setting of the tubing.

The process of the present invention further provides exposing the tubing to an ionizing dose of radiation to improve performance with medical infusion pumps.

BRIEF DESCRIPTION OF DRAWINGS

FIG. 1 is an enlarged cross-sectional view of a monolayer medical tubing of the present invention;

FIG. 2 is an enlarged cross-sectional view of a multi-layered tubing of the invention;

FIG. 2a is an enlarged cross-sectional view of a multi-layered tubing of the invention;

FIG. 3 is a schematic representation of a method for forming, surface modifying, orienting and heat setting medical tubing;

FIG. 3a is a plan view of a serpentine pattern that tubing may follow through a heating or cooling bath of the process shown in FIG. 3;

FIG. 3b is a schematic representation of a method for forming, dry orienting and heat setting medical tubing;

FIG. 6 is a graphical representation of the relationship between pump accuracy and cobalt-60 gamma radiation dosage;

DETAILED DISCLOSURE

Figure 4:
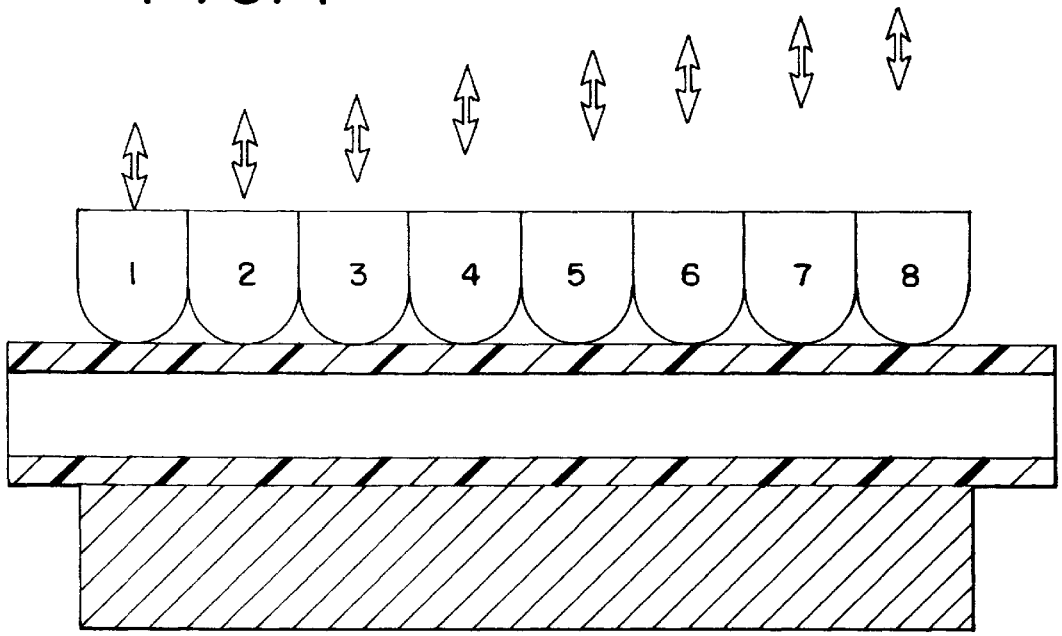
FIG. 4 is a schematic of a method of pumping fluid through polymeric tubing.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

I. Medical Tubing FIG. 1 shows a monolayer tubing structure 10 having a sidewall 12.

Preferably the tubing sidewall is fabricated from a polymeric material of an ethylene copolymerized with comonomers selected from the group consisting of lower alkyl olefins, and lower alkyl and lower alkene substituted carboxylic acids and ester and anhydride derivatives thereof. Preferably, the carboxylic acids have from 3–10 carbons. Such carboxylic acids therefore include acetic acid, acrylic acid and butyric acid. The term "lower alkene" and "lower alkyl" is meant to include a carbon chain having from 3–18 carbons more preferably 3–10 and most preferably 3–8 carbons. In one preferred form of the invention, the tubing is an ethylene and vinyl acetate copolymer having a vinyl acetate content of less than about 36% by weight, more preferably less than about 33% by weight and most preferably less than or equal to about 28% by weight. It is also preferred that the EVA have a high molecular weight and a melt flow index as measured by ASTM D-1238 of less than 5.0 g/10 minutes, more preferably less than about 1.0 g/10 minutes and most preferably less than 0.8 g/10 minutes or any range or combination of ranges therein.

In another preferred form of the invention, the tubing of the present invention is an ethylene copolymerized with alpha-olefins. The alpha-olefins may contain from 2 to about 20 carbon atoms or any range or combination of ranges therein. Alph-aolefins containing from 2 to about 10 carbon atoms are more preferred. Thus, the olefin polymers may be derived from olefins such as ethylene, propylene, 1-butene, 1-pentene, 4-methyl-1-pentene, 1-octene, 1-decene, 4-ethyl-1-hexene, etc., or mixtures of two or more of these olefins. Examples of particularly useful olefin polymers include ethylene-butene copolymers and ethylene and propylene copolymers, ethylene and hexene-1 copolymers and ethylene and octene-1 copolymers which will be referred to as ultra-low density polyethylenes (ULDPE). Such ULDPE's have a density of preferably equal to or below 0.910 g/cm$^3$ and preferably are produced using metallocene catalyst systems. Such catalysts are said to be "single site" catalysts because they have a single, sterically and electronically equivalent catalyst position as opposed to the Ziegler-Natta type catalysts which are known to have multiple catalysts sites. Such metallocene catalyzed ethylene α-olefins are sold by Dow under the tradename AFFINITY and by Dupont-Dow under the trade name ENGAGE, Phillips Chemical Company under the name MARLEX, and by Exxon under the tradename EXACT.

It may be desirable to add a radiation sensitive additive to the tubing material that is responsive to exposure to radiation such as gamma rays, electron beam, ultra-violet light, visible light or other ionizing energy sources. Suitable radiation sensitive additives include organic peroxides such as dicumyl peroxide (DiCup) and other free radical generating compounds. Other free-radical sensitive functional groups include acrylate, acid, dienes and their copolymers and terpolmyers, amide, amine, silane, urethane, hydroxyl, epoxy, ester, pyrolidone, acetate, carbon monoxide, ketone, imidazoline, photo and UV initiators, fluoro-compounds, etc. These functional groups may be in polymeric and non-polymeric compounds. More particularly suitable additives include ethylene vinyl acetate, ethylene methyl acrylate (EMA), ethylene acrylic acid (EAA), fatty amides, low viscosity functionalized and non-functionalized styrene-butadiene copolymers and their hydrogenated derivatives, functionalized and non-functionalized polybutadiene, polyisoprene, ethylene propylene diene monomer terpolymer, polybutene, urethane acrylate, epoxy acrylate, photoinitiators, etc. Even more particularly the additives include low viscosity functionalized ultra-low density polyethylene, functionalized with epoxys, carboxylic acids and their ester and anhydride derivatives, A-C polymers by Allied Signal, SR/CN and Esacure products from Sartomer, functionalized fatty products from Akzo Nobel and Henkel, photoinitiators from Ciba-Geigy, fluoro compounds from 3 M, EVA from DuPont, EAA from Dow Chemical and EMA from Chevron and 1,2-syndiotactic polybutadiene from Japan Synthetic Rubber Co. The ethylene-propylene terpolymers have a third component of a chain nonconjugated diolefin e.g. 1,4-pentadiene, 1,4-hexadiene, 1,5-hexadiene or a cyclic polyene e.g dicyclopentadiene, methylenenorbornene, ethylidenenorbornene, cyclooctadiene, methyltetrahydroindene, etc. These types of additives shall be referred to as EPDM.

Suitable EPDM's are sold under the tradenames NORDEL (Dupont Chemical Company), VISTALON (Exxon), KELTAN (Dutch State Mines), JSR (Japan Synthetic Rubber) and EPDM from Mitsui Chemical Company.

The radiation sensitive additives should be added to the tubing material in effective amounts preferably in an amount by weight of the monolayer or outer layer from 0.01–20.0%, more preferably from 0.01–10.0% and most preferably 0.02–5.0%.

FIG. 2a shows a multilayered tubing having outer layer 12, inner layer 14 and a core layer 15. In a preferred form, the outer layer 12 and the core layer 15 are constructed of the same material and additives as set forth above for the tubing materials. The outer and core layers 12 and 15 do not have to be of the same material as one another. Preferably the inner layer 14 or solution contact layer is selected from homopolymers and copolymers of alpha olefins. More preferably the inner layer 14 polyolefin is an ethylene copolymer with alpha olefins having from 3–18 carbons and more preferably from 4 to 8 carbons and most preferably is a ULDPE. Preferably, the inner layer has a minimum amount of components that are capable of migrating into a solution passing through the tubing 10. Also, the outer layer 12 should have a modulus of elasticity of less than the inner layer 14. In a preferred form, the core layer 15 will be the thickest layer and constitute from 55–99%, more preferably from 75–99% and most preferably from 90–98% of the total wall thickness or any range or combination of ranges therein.

In a two-layered tubing structure shown in FIG. 2, preferably the outer layer 12 should be thicker than the inner layer 14. Preferably the inner layer will have a thickness in the range of 1–40%, more preferably from 1–25% and most preferably from 2–10% of the total wall thickness or any range or combination of ranges therein.

II. Method of Fabricating Medical Tubing

The tubing of the present invention preferably is formed using extrusion and coextrusion techniques. The medical tubings 10 of the present invention should have an inner diameter dimension within the range of 0.003–0.4 inches, and an outer diameter dimension within the range of 0.12–0.50 inches. More particularly, medical tubing for use in the administration of fluid using a medical infusion pump, such as Baxter infusion pump sold under the tradename FLO-GARD®, and COLLEAGUE®, have an inner diameter within the range of 0.099–0.105 inches, an outer diameter within the range of 0.134–0.145 inches, and a wall thickness within the range of 0.018–0.021 inches. The tubing should be flexible having a modulus of elasticity of less than 50,000 psi, more preferably less than 30,000, even more preferably less than 10,000 and most preferably less than 4,000 psi, or any range or combination of ranges therein.

III. Method of Surface Modifying the Tubing

In a preferred form of the invention the surface of the tubing 10 is modified to increase the compatibility of the tubing with polar adhesives and to increase the surface lubricity of the tubing. By increasing the compatibility with adhesives the tubing can be more readily bonded to rigid medical housings fabricated from polar polymers such as polycarbonates, acrylics, polyesters and the like. The surface modification also increases the surface lubricity of the tubing so that a slide clamp can be used to regulate the flow of fluid through the tubing without severing the tubing. Further, the surface modification enhances performance of the tubing when used with medical infusion pumps.

Figure 9:
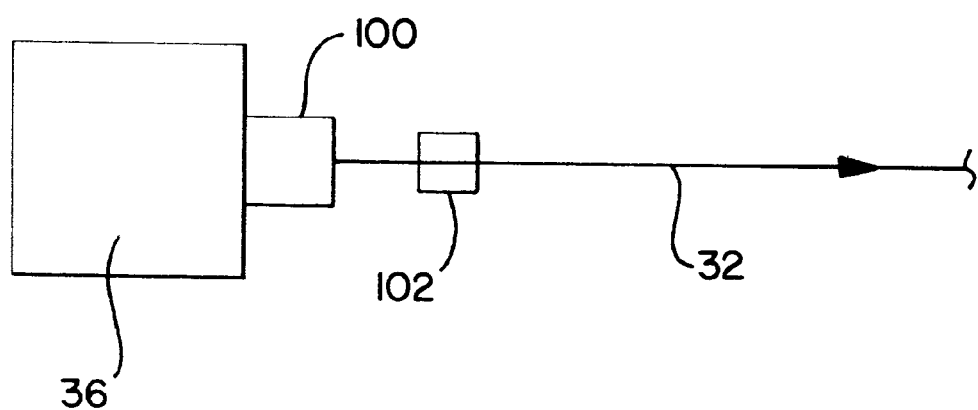
FIG. 9 is a schematic representation of surface modifying a tubing exiting an extruder die.

FIG. 9 shows the tubing 10 exiting an extruder 30 having extrusion die 100 and entering a station 102 where a preheated surface modifier solution is applied to the outer surface of the tubing. The surface modifier may be applied by any method that allows for relatively uniform application over the surface of the tubing. It is contemplated that the surface modifier may be applied by drawing the tubing through a bath of the solution. To accommodate varying extrusion line speeds the length of the bath may be changed or the concentration of the surface modifier in solution to achieve the desired surface modification. The surface modifier can also be applied by spraying the surface modifier under pressure, applying the modifier with a sponge, roller or brush or by other means well known in the art.

Unlike prior art attempts to surface modify tubing, the present invention provides for preheating the surface modifier solution and applying it to the tubing soon after the tubing exits the extrusion die and before the tubing has solidified or, in other words, while the tubing is in the molten or semi-molten state. Prior art coating processes known to the present inventors provided for spraying room temperature surface modifiers onto room temperature tubing in a solid state. In a preferred form of the invention, the surface modifier is preheated to a temperature of from about 30–95° C., more preferably from 40–85° C. and most preferably from about 50–80° C.

Suitable surface modifiers include both non-polymeric and polymeric compounds. Suitable non-polymeric additives can be selected from the group of non-polymeric aliphatic or aromatic hydrocarbons having greater than 5 carbon atoms but less than 500, more preferably less than 200 carbons and most preferably less than 100 carbons in the backbone. Further, the non-polymeric additives should have electron negative groups selected from the group of amines; amides; hydroxyls; acids; acetate, ammonium salts; organometallic compounds such as metal alcoholates, metal carboxylates, and metal complexes of numerous 1,3 dicarbonyl compounds; phenyl phosphines; pyridines; pyrrolidones; imidazoline, and oxazolines.

More preferably, the non-polymeric additives are selected from the group consisting of polyoxyethylene(5)oleylamine (Ethomeen 0/15, Akzo Nobel Chemical Company), bis(2-hydroxyethyl)soyaamine (Ethomeen S/12), bis(225-hydroxyethyl)oleylamine (Ethomeen 0/12), and polyoxyethylene(5)octadecylamine (Ethomeen 18/15).

Suitable polymeric surface modifiers include polyurethane, and copolymers of ethylene copolymerized with comonomers selected from the group consisting of lower alkyl substituted carboxylic acids, lower alkene substituted carboxylic acids, ester, anhydride and saponified derivatives thereof. Preferably, the carboxylic acids have from 3–10carbons. Such carboxylic acids therefore include acetic acid, acrylic acid and butyric acid. The term "lower alkene" and "lower alkyl" is meant to include a carbon chain having from 3–18 carbons more preferably 3–10 and most preferably 3–8 carbons. In a preferred form of the invention the polymeric additive is selected from the group of polyurethanes, ethylene vinyl acetate copolymers and ethylene vinyl alcohol copolymers.

The additives can be incorporated into solutions of water, ketones, aldehydes, aliphatic alcohols, freon, freon replacement solvents other common organic solvents and mixtures of the same. Suitable aliphatic alcohols include, but are not limited to, ethyl, isopropyl, tertiary butyl, and isobutyl. The additive solution can also include optional components such as emulsifiers, thickeners, thiners, colorants, antiblock agents and U.V. block agents. In a preferred form of the invention, the additive solution has from about 15% to about 50% by weight of a fatty amide incorporated into a 50:50 solution of water and isopropyl alcohol.

It is critical to apply the correct amount of additive to achieve both increased lubricity and increased bond strength with polar housings. To increase bond strength, the portion of the additive that is interacting with the adhesive must be anchored to the tubing outer layer. If too much additive is applied to the outer surface of the tubing, the portion of the additive that is interacting with the adhesive will not be anchored to the tubing and can slide along a portion of the additive that is anchored to the tubing.

In such an instance, the bond strength of the tubing to the housing will not be increased.

IV. Method of Heat Setting and Orienting the Tubing

Optionally, it may also desirable for the tubing 10 to be oriented along its longitudinal axis and set in this dimension using heat. This orientation step increases the yield strength of the tubing in the longitudinal direction thereby reducing the tendency for the tubing to neck during use. In effect, pre-orienting of the tubing increases the resistance to further necking. Preferably, the tubing 10 should be oriented so that the initial inner and outer diameters of the tubing are anywhere from 10%–300% greater than the diameter of the tubing 10 after orienting and more preferably from 20%–120% and most preferably from 30%–100%. These ranges further include all combinations and subcombinations of ranges therein. The ratio of the beginning diameter to the diameter after orienting shall be referred to as the orientation ratio. The orientation process may be a wet orientation process or a dry one as set forth below.

FIG. 3 shows a schematic representation 30 of the method of orienting the tubing 10 in a wet orientation process. The method of wet orienting includes the steps of providing a tubing 10, and orienting the tubing 10 along its longitudinal axis so that the tubing 10 has a desired inner and outer diameter, as specified above in Section II, and orientation ratio. It is believed that the orienting step aligns the molecules of the tubing along the longitudinal axis to increase the resistance to necking upon subsequent longitudinal stressings. The tubing 10 is then heat set to reduce shrinkage of the tubing and to fix the tubing in the oriented dimension.

The tubing 10 (which may be a single layered or multilayered) is pulled in a direction indicated by arrows 34 along a continuous path that may be referred to as a line. The term "up-line" shall refer to locations along the line in a direction opposite the direction to the flow of the tubing 32. Conversely, the term "down-line" shall refer to locations in the direction of the flow of the tubing. By using the term "line" it should not be thought that the method must be carried out in a straight line, rather it should be taken to mean that the method is carried out in a sequence of consecutive steps.

As shown in FIG. 3, tubing 10 is formed with an extruder 36. The tubing 32 exiting the extruder 36 preferably has an outer diameter dimension that will be from 10%–300% greater than after orienting and more preferably from 20%–120%, and most preferably from 30%–100% greater. The tubing 10 is pulled from the extruder 36 with a first puller 37, a second puller 38, a third puller 39, and a fourth puller 40.

The diameter of the tubing at the first puller 37, when the tubing is in a solid state, shall be referred to as the initial diameter. The pullers 37, 38, 39 and 40 may have a silicone or rubber coating to increase the coefficient of friction with the tubing 32.

The second and third pullers 38 and 39 may have a plurality of axially spaced and circumferentially extending grooves to accommodate more than one set of tubing 32 on a surface of the pullers 38 and 39 at a time.

After exiting the extruder 36, the tubing 32, which is in a molten or semi-molten phase, passes through a first cooling bath 41 where the tubing 32 is cooled with air or a liquid. Preferably, the first cooling bath 41 is a water bath at a temperature within the range of 4° C.–45° C. The tubing should be converted to a solid phase in the cooling bath 41.

After exiting the first cooling bath 41 the tubing 10 extends between the first and second pullers 37 and 38 where the tubing 10 is oriented by operating the second puller 38 at a greater rate of speed than the first puller 37 to achieve the desired orientation ratio. It is believed that orienting the tubing while in the solid state is more effective in achieving an oriented tubing than by stretching the tubing immediately after exiting the extruder 36 or as it is passes through the first cooling bath 41 while the tubing is in a molten or semi-molten phase. This section of the line will be referred to as the orienting section 42. Preferably the second puller 38 is operated at a rate within the range of about 4–10 times faster than the first puller 37. By controlling the relative speeds of the first and second pullers 37 and 38 one can control the final inner and outer diameters of the tubing 10 and achieve the desired orientation ratio.

In the orienting section 42 the tubing 10 is passed through a second cooling bath 43 where the tubing 10 is cooled with air or a liquid. Preferably, the second cooling bath 43, as the first cooling bath 41, is an aqueous bath at a temperature within the range of 4° C.–45° C.

To overcome the memory effect of the oriented tubing 10, it is necessary to heat the tubing to a temperature above that which it will normally be exposed during shipping, storage and use, but below the temperature at which the tubing is fully melted. By exposing the tubing to temperatures above the application temperature, less ordered lower melting crystals are melted leaving higher melting crystals which will be thermally stable over the application temperature range. Part of the highly oriented macro-molecule chains will be relaxed to provide a tubing with enhanced thermal stability.

To this end, after exiting the second cooling bath 43, the tubing 10 trains about the second puller 38 and extends between the second puller 38 and the third puller 39.

The tubing 10 proceeds in a direction back toward the extruder 36 and through a heating bath 44 where the tubing is heat set. Preferably, the heat bath 44 is positioned above the second cooling bath 43 to save floor space. However, this positioning is optional. This portion of the process will be referred to as the heat setting section or step 45. Preferably, the heat setting step 45 is done on-line after the orienting section 42, but could be done off-line in a batch mode process. During the heat setting step 45, the tubing 10 is passed through a heating bath 44 where the tubing 10 is heated with a medium such as heated air or liquid. The heating bath 44 preferably is an aqueous solution of water at a temperature of between about 50–99° C. Additives such as salt may be added to the aqueous solution.

In order to control the dimension of the tubing, it is desirable that the tubing 10 not be oriented during the heat setting step 45. For this reason the tubing 10 should be kept under minimum tension to keep the tubing taught or the tubing should be allowed to sag an amount, between the second and third pullers 38 and 39, to prevent or control the shrinkage. Thus, the second and third pullers 38 and 39 should be operated at similar speeds or puller 39 could be operated at a slightly slower speed than puller 38 to accommodate some shrinkage.

To further prevent orienting of the tubing 10 in the heat setting section 45, it may also be desirable to support the tubing 10 while being pulled through the heating bath 44 with a supporting structure 47. However, providing the supporting structure 47 is optional. Suitable supporting structures 47 include a conveyor that moves at the same rate of speed as the tubing 10 through the heating setting section 45. Another supporting structure 47 is a plastic or metal conduit having a diameter greater than that of the tubing wherein the tubing 10 is supported by the interior surface of the conduit.

After exiting the heating bath 44, the tubing 10 extends between the third puller 39 and the fourth puller 40. Puller 40 should be operated at a similar speed of puller 39 or slightly slower than 39 to prevent further orientation. The tubing 10 is passed again through the second cooling bath 43. Of course it is possible to provide for a separate cooling bath, but this arrangement saves floor space.

It may also be desirable to provide for the tubing 10 to make several lengthwise passes through the cooling bath 43 or heating bath 44 as shown in FIG. 3*a* to provide for maximum cooling or heating of the tubing in a minimal amount of space. This may be accomplished by providing a plurality of spaced rollers 49 to define a serpentine pattern through the heating bath 44 or cooling bath 43.

To prevent any further orientation of the tubing 10, it may be necessary to operate the fourth puller 40 at a similar speed or slightly slower rate of speed than the third puller 39.

After passing the fourth puller 40, the tubing has an oriented diameter and passes through a cutter or spool 48 where the tubing 10 is cut to the appropriate length or wrapped about the spool for storage or shipment.

FIG. 3b shows a dry orientation process 30. The dry orientation process is same in most respects to the wet orientation process with the major exception that the tubing 10 is oriented in section 42 between pullers 37 and 37a. Puller 37a is operated at a speed greater than puller 37. During the dry orientation step 42, the tubing 10 is not submerged in the aqueous bath 43 as is the case in the wet orientation step 42. In the dry orientation process, pullers 38, 39, and 40 will be run at a rate similar to or slower than puller 37a. Notwithstanding these differences between the wet and the dry orientation process, it is desirable that the tubing is oriented while in the solid state.

V. Method of Irradiating the Tubing

Figure 7A:
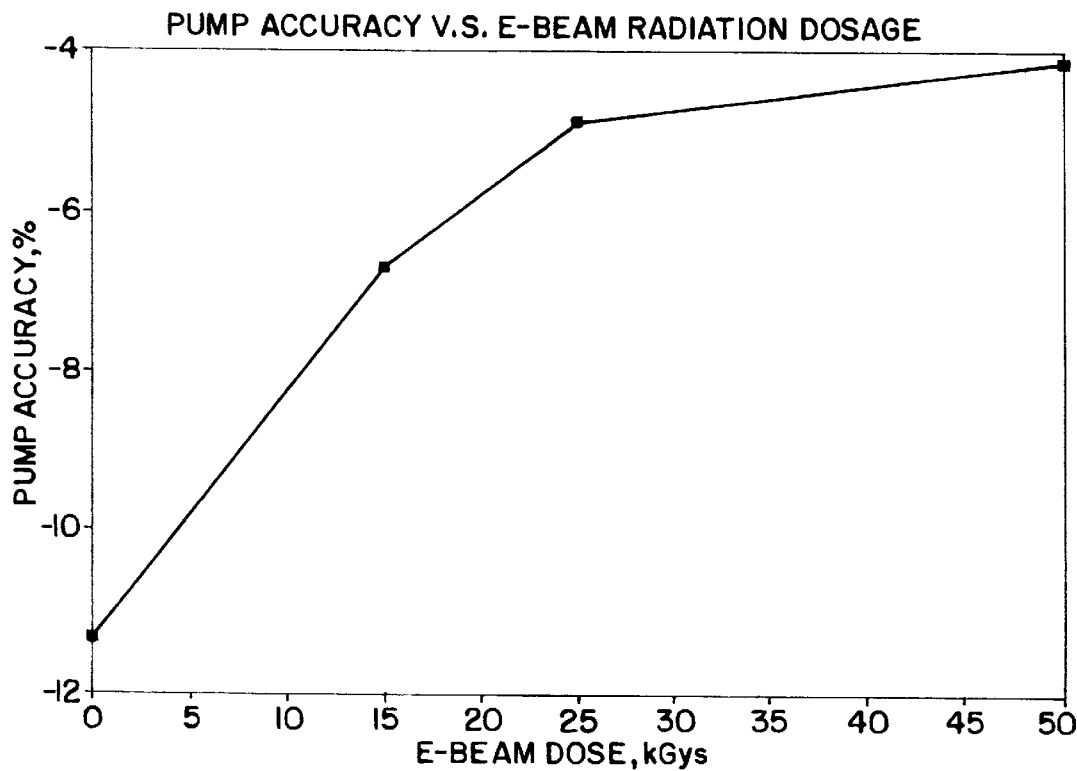
FIG. 7a is a graphical representation of the relationship between pump accuracy and electron beam radiation dosage.
Figure 7B:
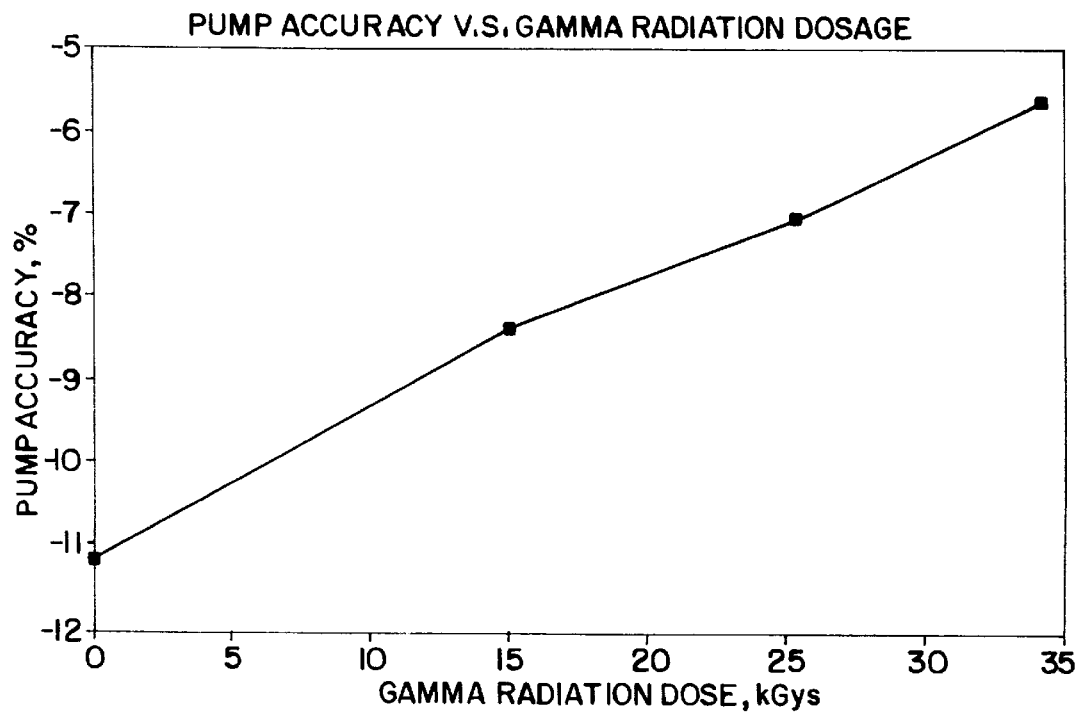
FIG. 7b is a graphical representation of the relationship between pump accuracy and gamma radiation dosage.
Figure 8A:
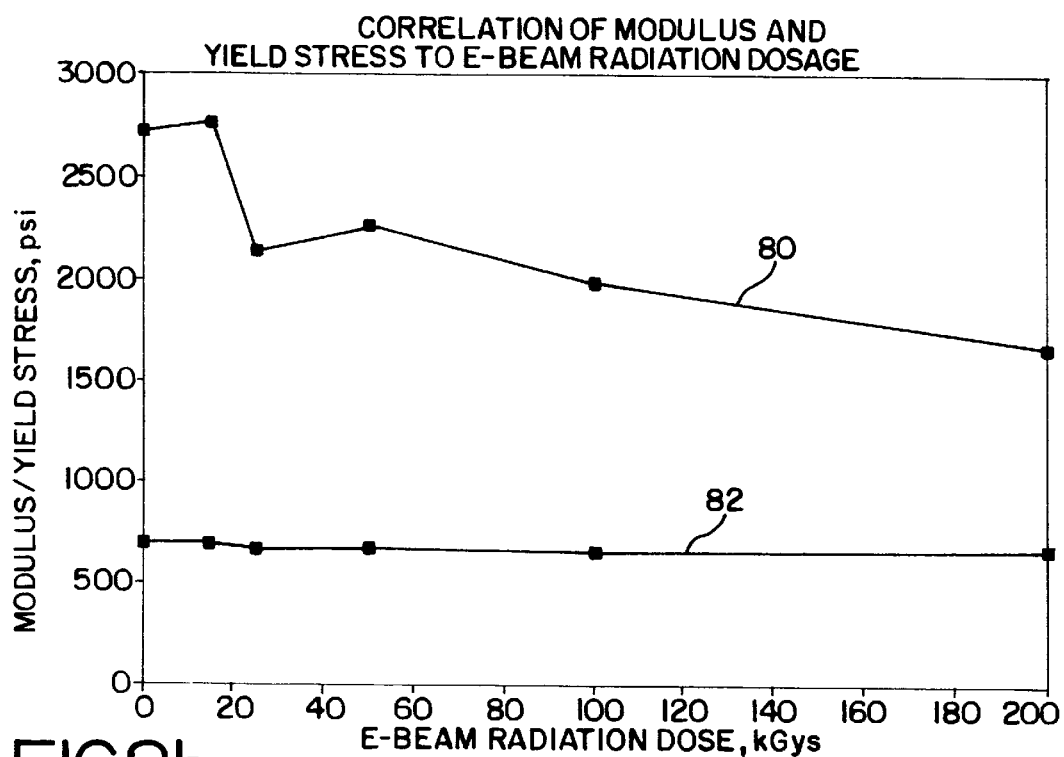
FIG. 8a is a graphical representation of the correlation between modulus of elasticity and yield strength with varying electron beam radiation dosages.
Figure 8B:
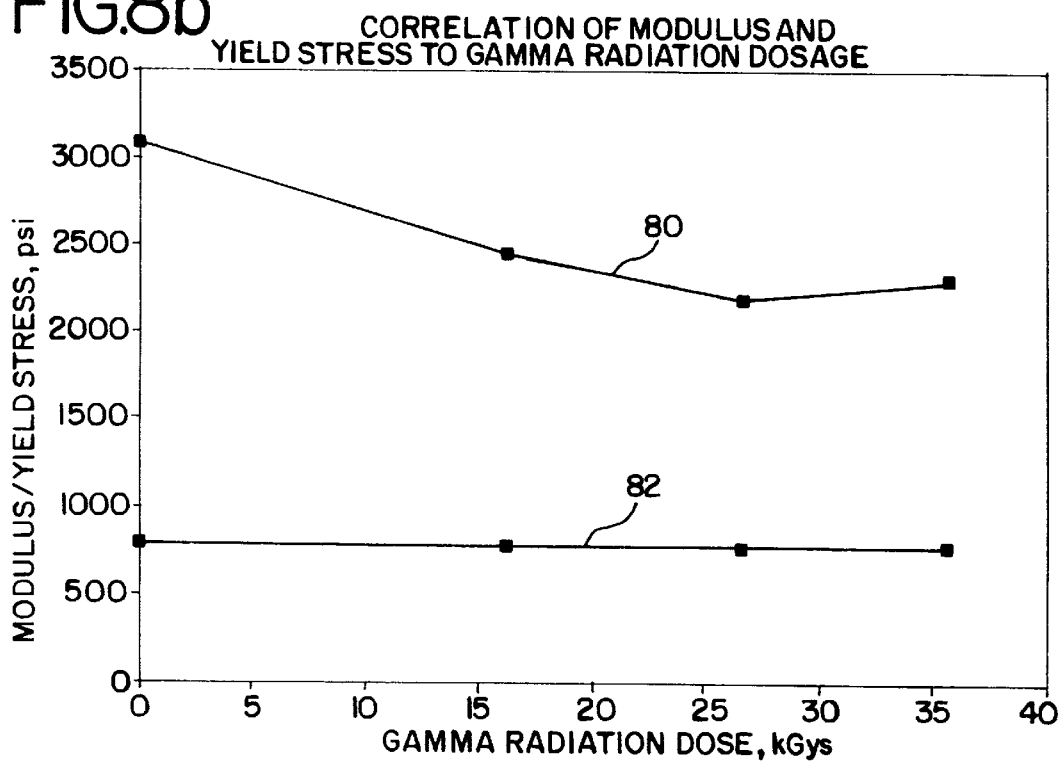
FIG. 8b is a graphical representation of the correlation between modulus of elasticity and yield strength with varying gamma radiation dosages.

During the course of medical device manufacturing, most medical devices have to be sterilized. Radiation sterilization is a preferred method. Surprisingly, it has been found in this investigation that by exposing the tubing to standard sterilization dosages of radiation, the tubing performance as measured by accuracy of fluid dosage delivery was improved. As shown in FIGS. 8a and 8b, pump accuracy increased with increasing dosages of e-beam radiation (FIG. 7a) and gamma radiation (FIG. 7b).

As shown in FIGS. 8a and 8b, it was also found that the modulus of elasticity of the tubing, line 80, decreased with increasing dosages of e-beam (FIG. 8a) and gamma radiation dosages (8b). It was surprising that these decreases in modulus were not accompanied by a significant decrease in yield strength of the tubing as indicated by line 82.

Sterilization radiation is typically carried out at much lower doses of radiation than are used to cross-link polymers. The typical magnitude of such sterilization radiation is on the order of about 25 kGys, but can sometimes be as low as 15kGys.

In some instances, although not necessarily, exposing the tubing to radiation sterilization results in a measurable change in gel content of the tubing. Gel content indicates the percentage of the weight of insolubles to the weight of the tubing material. This definition is based on the well-accepted principle that cross-linked polymer materials are not dissolvable. However, significant gel content such as about 50% renders the material a thermoset. Such thermosets are undesirable for medical usages as they are not capable of recycling using standard recycling techniques.

It is important to note that it is possible to expose tubing to sterilization dosages of radiation and achieve enhanced tubing performance with pumps without observing any changes in the gel content of the tubing. The medical tubing 10 of the present invention exhibits a gel content preferably ranging from 0% to 49.9%, more preferably 0% to 45%, and most preferably 0% to 40%, or any range or combination of ranges therein. Preferably, the tubing is exposed to a low dose of gamma radiation ranging from 15 kGys to 58 kGys, more preferably 15 kGys to 45 kGys, and most preferably 15 kGys to 35 kGys, or any range or combination of ranges therein. Thus, this tubing 10 maintains its thermoplastic characteristics and can be reprocessed or recycled using standard recycling techniques.

Pump accuracy can also be improved after even lower doses of radiation when very minute amounts of the radiation-sensitive additives described above are added to the polymeric material prior to extrusion.

An example of a pump in which an improvement in tubing performance has been observed is the FLO-GARD® 6201. The FLO-GARD® 6201 is a single pump head, electromechanical, positive pressure, peristaltic, intravenous, infusion device. The pump is designed to operate with standard PVC intravenous tubing that conforms to Baxter specifications. The pump has a primary flow rate range from 1 to 1999 mL/hr. The secondary range is 1 to 999 mL/hr, or the upper limit will be the same as the primary rate limit, which ever is lower. Infusible volume for both secondary and primary modes is 1 to 9999 mL. This pump has the capability of operating with a wide variety of standard I.V. administration sets including: basic sets, filter sets, CONTINU-FLO®and BURETROL® sets. The pump accuracy should be within ±10% for any flow rate setting during 24 hours of continuous service using the same I.V. administration set.

Figure 5:
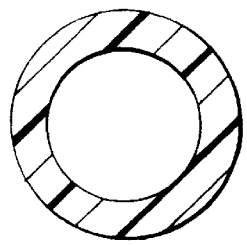
FIG. 5 is a cross sectional view of a polymeric tubing during an up-stroke in a pumping operation.
Figure 5A:
FIG. 5a is a cross-sectional view of a polymeric tubing during a down-stroke in a pumping operation.
Figure 5B:
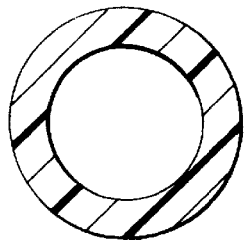
FIG. 5b is a cross-sectional view of a polymeric tubing prior to multiple compressions by a pump.
Figure 5C:
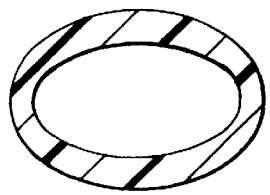
FIG. 5c is a cross-sectional view of a polymeric tubing after multiple compressions with a pump.

As depicted in FIG. 5, the pump has a series of eight "fingers." The fingers provide positive pressure to squeeze fluid out of the pump segment for delivery to the patient. The eight fingers move up and down in sequence and perform a peristaltic infusion function. During this process, the tubing undergoes repetitive cyclic deformations which eventually may cause permanent deformation in the tubing geometry. (See FIGS. 5a and 5b). This permanent deformation (See FIGS. 6 and 7) leads to a volumetric reduction in the tubing which, in turn, causes an under-delivery of fluid to the patient. Such phenomenon is generally referred to as "pump fall-off."

The Examples below will show that the tubing of the present invention had less change in flow-rate over a 72 hour period when compared to non-radiation sterilized tubing and existing PVC medical tubing. Illustrative, non-limiting examples of the present tubings are set out below. Numerous other examples can readily be envisioned in light of the guiding principles and teachings contained herein. The examples given herein are intended to illustrate the invention and not in any sense to limit the manner in which the invention can be practiced.

VI. Examples

Bilayer tubing was coextruded having an outer layer of ethylene vinyl acetate copolymer (DuPont CM-576) with an inner layer of metallocene catalyzed ULDPE (Dow Engage 8401). The outer layer was extruded using a 1.5 inch Davis Standard extruder having 4 barrel zones at 390° F. and 3 die zones having a temperature of 390° F. The inner layer was extruded on a 1 inch Davis Standard having 3 barrel zones and 2 die zones at 340° F. The tubing had an inner diameter of 0.103 inches and an wall thickness of 0.0195 inches. Upon exiting an extrusion die of the extruder, the tubing was drawn through a heated bath containing Ethomeen 0/15having a concentration of from 15%–50% by weight in a 50:50 solution of water and isopropyl alcohol. The solution was heated to 60° C. The tubing was cut into approximately 6 inch lengths.

The tubing was tested for bond strength, pump compatibility and slide clamp compatibility.

To test the bond strength, a set of tubing segments were gamma sterilized at 35.1 kGys. The tubing segments were attached to polycarbonate housings with a cyanoacrylate adhesive and pulled until break. The forced required to break the tubing was measured by an Instron tester. The results of these tests are set forth below in Table 1.

TABLE 1

| | | Gamma Sterilized 35.1 kGy | | |
|---|---|---|---|---|
| Sample No. | Concentration of Additive | Bonding Force, lb. Ave. | Std. Dev. (N = 10) | Min. pull force, lb. |
| 1 | 15 | 10.2 | 0.33 | 9.5 |
| 2 | 20 | 9.5 | 0.50 | 8.7 |
| 3 | 25 | 9.8 | 0.36 | 9.1 |
| 4 | 30 | 9.2 | 0.31 | 8.7 |
| 5 | 50 | 7.6 | 2.24 | 3.8 |

To test pump compatibility, sections of tubing were inserted into a Baxter COLLEAGUE™ pump. The pump has sensor to detect air bubbles. If the tubing has insufficient contact with the sensor housing, which will occur if the tubing has insufficient lubricity, the sensor will sound a fault alarm and will not allow the pump to be activated. Tubing was coextruded as set forth above and drawn through a bath having 15 weight percent Ethomeen 0/15 and heated to 60° C. The tubing was not gamma sterilized. All tubing was found to have sufficient lubricity to allow initiating of the pump.

These sections of tubing were also subjected to multiple uses of a slide clamp without significant damage to the tubing.

While specific embodiments have been illustrated and described, numerous modifications are possible without departing from the spirit of the invention, and the scope of protection is only limited by the scope of the accompanying claims.

We claim:

1. A method for fabricating a medical tubing comprising the steps of:
   providing a material selected from the group consisting of ethylene homopolymers and ethylene copolymers, wherein the ethylene copolymers are obtained by copolymerizing ethylene with a comonomer selected from the group consisting of lower alkyl olefins, lower alkyl esters of a carboxylic acid and lower alkene esters of a carboxylic acid, or blends thereof;
   providing an extruder with an extrusion die;
   extruding the material into a medical tubing;
   providing a surface modifier solution;
   preheating the surface modifier solution to a temperature within the range of 30–95° C.; and
   applying the preheated solution onto the tubing at it exits the extrusion die when the tubing is in a molten state or a semi-molten state.

2. The method of claim 1 further comprising the step of exposing the tubing to a sterilization dosage of radiation of from about 15 to about 45 kGys.

3. The method of claim 2 wherein the step of exposing the tubing to sterilization dosage of radiation comprises the step of exposing the tubing to a source of radiation selected from the group consisting of gamma rays, ultra-violet rays, and electron beam.

4. The method of claim 1 wherein the material is an ethylene vinyl acetate copolymer having a vinyl acetate content of not more than 36% vinyl acetate by weight of the copolymer.

5. The method of claim 4 wherein the ethylene vinyl acetate copolymer has a melt flow index of less than about 5.0 g/10 minutes.

6. The method of claim 4 wherein the ethylene vinyl acetate copolymer has a melt flow index of less than about 1.0 g/10 minutes.

7. The method of claim 6 wherein the ethylene vinyl acetate copolymer has a melt flow index of less than about 0.80 g/10 minutes.

8. The method of claim 1 wherein the material is an ethylene and alpha olefin copolymer.

9. The method of claim 8 wherein the ethylene and alpha olefin copolymer has a density less than 0.910 g/cc.

10. The method of claim 9 wherein the ethylene and alpha olefin copolymer is obtained using a metallocene catalyst.

11. The method of claim 1 wherein the surface modifier solution includes as a component selected from the group consisting of an aliphatic or aromatic hydrocarbon having greater than 5 carbon atoms but less than 500 and an electron negative group selected from the group of amines; amides; hydroxyls; acids; acetate, ammonium salts; organometallic compounds such as metal alcoholates, metal carboxylates, and metal complexes of numerous 1,3 dicarbonyl compounds; phenyl phosphines; pyridines; pyrrolidones; imidazoline, and oxazolines.

12. The method of claim 11 wherein the hydrocarbon has less than 200 carbons.

13. The method of claim 11 wherein the hydrocarbon has less than 100 carbons.

14. The method of claim 13 wherein the functional group is an amide.

15. The method of claim 14 wherein the component is selected from the group consisting of polyoxyethylene(5) oleylamine, bis(2-hydroxyethyl)soyaamine, bis(2-hydroxyethyl)oleylamine, and polyoxyethylene(5) octadecylamine.

16. The method of claim 1 wherein the surface modifier solution includes as a component selected from the group consisting of polyurethane, and copolymers of ethylene copolymerized with comonomers selected from the group consisting of lower alkyl substituted carboxylic acids, lower alkene substituted carboxylic acids, ester, anhydride and saponified derivatives thereof.

17. The method of claim 11 wherein the surface modifier solution further comprises a solvent containing a member selected from the group consisting of water, ketones, aldehydes, aliphatic alcohols, freon, and freon replacement solvents.

* * * * *